United States Patent
Kimura et al.

(10) Patent No.: US 8,447,382 B2
(45) Date of Patent: May 21, 2013

(54) POSITIONING SYSTEM AND METHOD OF POSITION DETECTING

(75) Inventors: Atsushi Kimura, Akiruno (JP); Ryoji Sato, Fuchu (JP); Atsushi Chiba, Hachioji (JP); Takahiro Iida, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 182 days.

(21) Appl. No.: 12/787,705

(22) Filed: May 26, 2010

(65) Prior Publication Data

US 2010/0305426 A1    Dec. 2, 2010

Related U.S. Application Data

(63) Continuation of application No. PCT/JP2009/069960, filed on Nov. 26, 2009.

(30) Foreign Application Priority Data

Nov. 28, 2008   (JP) ................................ 2008-305621

(51) Int. Cl.
    *A61B 5/05*   (2006.01)
(52) U.S. Cl.
    USPC ........................... 600/424; 600/327; 600/423
(58) Field of Classification Search
    USPC ................ 600/327, 332, 342, 407, 409, 410, 600/420, 422, 423, 424, 431; 73/1.41, 1.54, 73/1.55
    See application file for complete search history.

(56) References Cited

U.S. PATENT DOCUMENTS

| | | | |
|---|---|---|---|
| 2005/0216231 A1 | 9/2005 | Aoki et al. | |
| 2006/0122493 A1* | 6/2006 | Atalar et al. | 600/423 |
| 2007/0083257 A1* | 4/2007 | Pal et al. | 623/1.22 |
| 2007/0185398 A1* | 8/2007 | Kimura et al. | 600/424 |
| 2007/0244388 A1* | 10/2007 | Sato et al. | 600/424 |

(Continued)

FOREIGN PATENT DOCUMENTS

| | | |
|---|---|---|
| JP | 62-175687 A | 8/1987 |
| JP | 2005-245963 A | 9/2005 |

(Continued)

OTHER PUBLICATIONS

International Search Report dated Feb. 16, 2010.

*Primary Examiner* — James Kish
*Assistant Examiner* — Michael N Fisher
(74) *Attorney, Agent, or Firm* — Scully, Scott, Murphy & Presser, P.C.

(57) ABSTRACT

A body-insertable device including a resonance circuit for emitting a resonance magnetic field by being induced by a drive magnetic field received from the outside. An external device for deriving position information of the resonance circuit by using a detection signal of detected resonance magnetic field. The external device includes a drive coil driving unit for outputting a drive signal having a predetermined frequency, a drive coil for receiving the output drive signal and generating the drive magnetic field, and a drive magnetic field generation control unit for calculating an amplitude value of the drive signal by using a current amplitude value of the drive signal, detecting a degree of stability indicating whether a sharp change occurs in the drive magnetic field based on the calculated amplitude value, and controlling the deriving of a position information based on the detected degree of stability in the drive magnetic field.

14 Claims, 12 Drawing Sheets

U.S. PATENT DOCUMENTS

| | | |
|---|---|---|
| 2008/0177177 A1 | 7/2008 | Aoki et al. |
| 2008/0177178 A1 | 7/2008 | Aoki et al. |
| 2008/0281188 A1 | 11/2008 | Aoki et al. |
| 2009/0177036 A1 | 7/2009 | Shimizu et al. |
| 2009/0295386 A1 | 12/2009 | Sato et al. |
| 2010/0052972 A1 | 3/2010 | Kasano et al. |

FOREIGN PATENT DOCUMENTS

| | | |
|---|---|---|
| JP | 2006-034678 A | 2/2006 |
| JP | 2006-271520 A | 10/2006 |
| JP | 2008-145255 A | 6/2008 |
| WO | WO 2007/043458 A1 | 4/2007 |
| WO | WO 2007/069483 A1 | 6/2007 |

* cited by examiner

POSITIONING SYSTEM AND METHOD OF POSITION DETECTING

CROSS-REFERENCE TO RELATED APPLICATIONS

This application is a continuation of PCT international application Ser. No. PCT/JP2009/069960 filed on Nov. 26, 2009 which designates the United States, which claims the benefit of priority to JP 2008-305621, filed on Nov. 28, 2008, the contents of which are incorporated herein by reference.

BACKGROUND OF THE INVENTION

1. Field of the Invention

The present invention relates to a position detecting system and a method of position detection and, more particularly, to a position detecting system and a method of position detection, for detecting the position of a capsule body-insertable apparatus which is introduced in a subject by using a magnetic field.

2. Description of the Related Art

In recent years, a capsule body-insertable apparatus having an imaging device (hereinbelow, called a "capsule endoscope") is developed. The capsule endoscope is introduced into a subject, for example, via the oral route, captures an image of the inside of the subject, and transmits the obtained image (hereinbelow, called an "in-vivo image") to an apparatus disposed on the outside of the subject by radio. The operator can diagnose a symptom or the like by visually recognizing the in-vivo image received by the outside apparatus.

Such a capsule endoscope usually cannot move in a subject by itself and is moved in a subject by peristaltic movement of digestive organs of the subject. Consequently, there is a case such that, for example, as compared with an endoscope in which an observation region can be selected by the operator freely to a certain degree such as a fiber scope, the observation capability of the capsule endoscope is lower.

An example of techniques for solving such a drawback is the technique disclosed in Japanese Laid-open Patent Publication No. 2005-245963. According to the conventional art, by applying a magnetic field (hereinbelow, called a "guidance magnetic field") from the outside of a subject to a capsule endoscope having magnetic field generating means such as a permanent magnet, the posture and movement of the capsule endoscope can be positively controlled from the outside of the subject.

In order to control the posture and movement of the capsule endoscope in the subject by the magnetic field applied from the outside of the subject like in the conventional art, however, the position, direction, and the like of the capsule endoscope in the subject have to be known accurately. In the following, detection of the position and direction (posture) of the capsule endoscope will be simply called position detection.

In the conventional art, by providing a resonance circuit having a coil (L) and a capacitor (C) (hereinbelow, called an "LC resonance circuit") in the capsule endoscope. The LC resonance circuit detects a resonance magnetic field generated by a magnetic field applied from the outside (hereinbelow, called a "drive magnetic field"), thereby detecting the position and direction of the capsule endoscope. In the following, the method of deriving information of the position, direction, and the like from the resonance magnetic field generated by applying the drive magnetic field to the LC resonance circuit from the outside will be called a passive method. The passive method has an advantage such that power consumption of the capsule endoscope can be suppressed.

SUMMARY OF THE INVENTION

A position detecting system according to an aspect of the present invention includes a body-insertable apparatus disposed in a state where it is introduced in a subject in a detection space; and an external device disposed on the outside of the subject. The body-insertable apparatus includes a resonance circuit for emitting a resonance magnetic field by being induced by a drive magnetic field received from the outside. The external device includes a drive coil driving unit for outputting a drive signal having a predetermined frequency; a drive coil for receiving the output drive signal and generating the drive magnetic field in the detection space; a sense coil for detecting the resonance magnetic field and outputting a detection signal; a position deriving unit for deriving position information of the resonance circuit by using the detection signal; a current detecting unit for detecting a current amplitude value of the drive signal input to the drive coil; and a drive magnetic field generation control unit for calculating an amplitude value of a drive signal which is to be output to the drive coil driving unit by using the current amplitude value, detecting a degree of stability indicating whether a sharp change occurs in the drive magnetic field on the basis of the calculated amplitude value, and controlling the position deriving unit on the basis of the detected degree of stability in the drive magnetic field detected.

A method of position detection according to another aspect of the present invention is a method for detecting position, in a subject, of a body-insertable apparatus having a resonance circuit for emitting a resonance magnetic field by being guided by a drive magnetic field received from the outside. The method includes a drive magnetic field generating step of generating the drive magnetic field by inputting a drive signal having a predetermined frequency to a drive coil; a resonance magnetic field detecting step of detecting the resonance magnetic field; a position deriving step of deriving position information of the body-insertable apparatus from the resonance magnetic field detected in the resonance magnetic field detecting step; a current detecting step of detecting a current amplitude value of the drive signal input to the drive coil; and a drive magnetic field generation control step of calculating an amplitude value of a drive signal which is input to the drive coil by using the current amplitude value, detecting the degree of stability indicating whether a sharp change occurs in the drive magnetic field on the basis of the calculated amplitude value, and controlling the position deriving unit on the basis of the detected degree of stability in the drive magnetic field.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
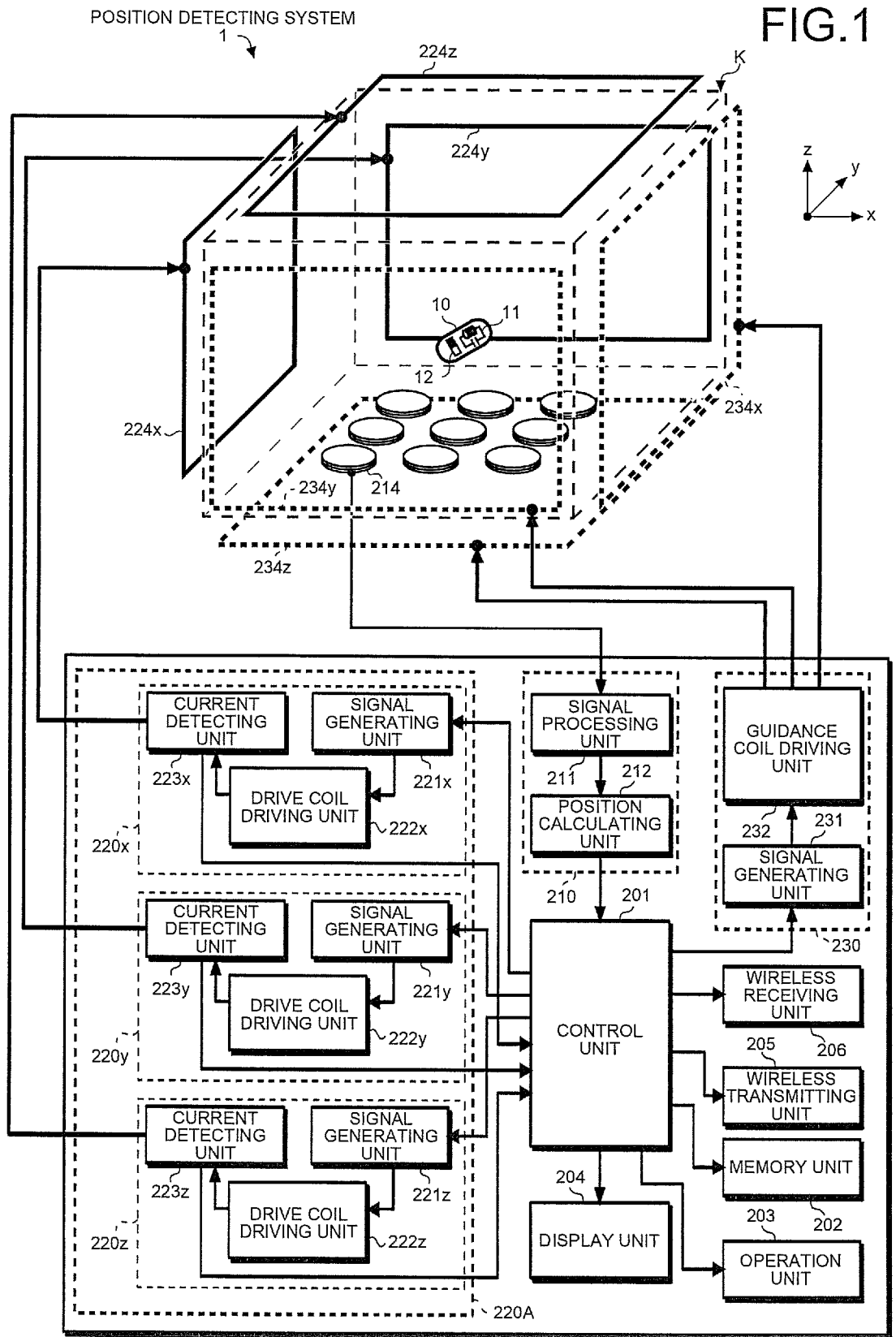
FIG. 1 is a schematic diagram showing a schematic configuration of a position detecting magnetic guidance system according to a first embodiment of the present invention.

Some modes for carrying out the present invention will be described in detail below with reference to the drawings. In the following description, the drawings just schematically show shapes, sizes, and positional relations to a degree that the content of the present invention can be understood. Therefore, the present invention is not limited to the shapes, sizes, and positional relations shown in the drawings. In the drawings, to clearly show the configuration, a part of hatching in cross sections is omitted. Further, numerical values exemplified in the following description are just preferable examples of the invention. Therefore, the invention is not limited to the numerical values exemplified.

First Embodiment

In the following, the configuration and operation of a position detecting magnetic guidance system 1 according to a first embodiment of the invention will be described in detail with reference to the drawings. The embodiment is directed to avoid increase in an error included in a derived position detection result at the time of feedback controlling a drive magnetic field generating apparatus 220A which will be described later (refer to FIG. 1), thereby stably enabling accurate position detection in the position detecting magnetic guidance system 1 using the feedback control.

Configuration

FIG. 1 is a schematic diagram showing a schematic configuration of the position detecting magnetic guidance system 1 according to the first embodiment. As shown in FIG. 1, the position detecting magnetic guidance system 1 has a detection space K enclosing a subject in which a capsule medical apparatus 10 as a body-insertable apparatus is introduced, and an external device 200 that detects the direction and orientation (posture) of the capsule medical apparatus 10 in the detection space K and guiding the capsule medical apparatus 10 in a direction and orientation desired by the operator.

Capsule Medical Apparatus

Figure 2:
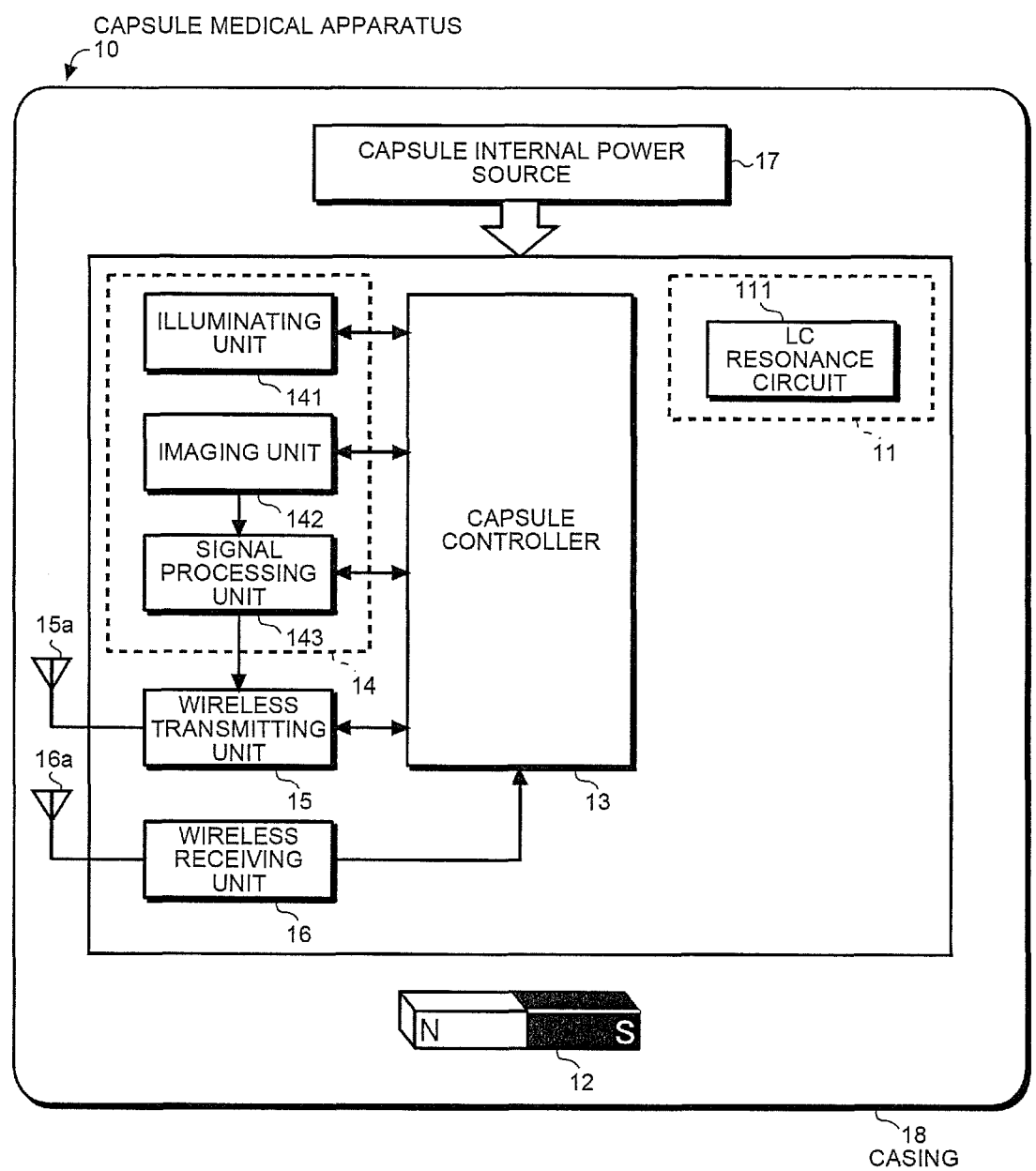
FIG. 2 is a block diagram showing a schematic configuration of a capsule medical apparatus according to the first embodiment or a second embodiment of the present invention.

The capsule medical apparatus 10 includes not only a resonance magnetic field generator 11 for generating resonance magnetic field for position detection and a magnetic field generator 12 (refer to FIG. 1) for guiding the capsule medical apparatus 10 by using an external magnetic field (guidance magnetic field which will be described later) but also, as shown in FIG. 2, for example, a capsule controller 13 for controlling the parts in the capsule medical apparatus 10, an in-vivo information acquiring unit 14 for acquiring various information in the subject; a wireless transmitting unit 15 and a transmitting antenna 15a for transmitting in-vivo information acquired by the in-vivo information acquiring unit 14 as wireless signals to the outside of the capsule medical apparatus 10; a wireless receiving unit 16 and a receiving antenna 16a for receiving various operation instructions and the like transmitted as wireless signals from the external device 200; and a capsule internal power source 17 for supplying power to the components in the capsule medical apparatus 10.

The in-vivo information acquiring unit 14 includes an imaging unit 142 for acquiring an in-vivo image as in-vivo information; an illuminating unit 141 for illuminating the inside of the subject at the time of imaging the inside of the subject by the imaging unit 142; and a signal processing unit 143 for executing a predetermined signal process on the in-vivo image acquired by the imaging unit 142.

Figure 3:
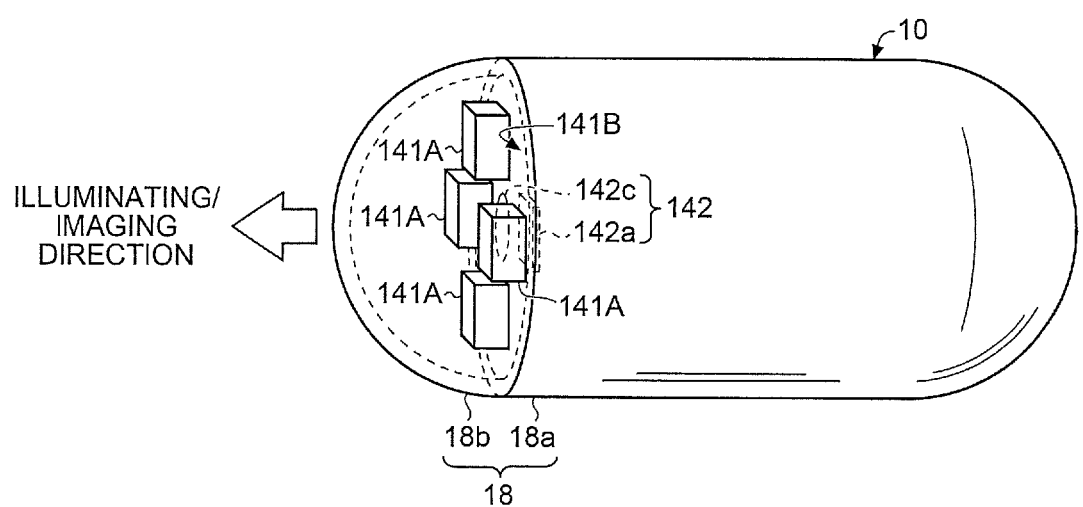
FIG. 3 is an appearance view showing a schematic configuration of the capsule medical apparatus according to the first or second embodiment of the invention.

The imaging unit 142 includes, for example, as shown in FIG. 3, an imaging device 142a for converting incident light to an electric signal and forming an image, an objective lens 142c disposed on a light reception plane side of the imaging device 142a, and a not-shown imaging device drive circuit for driving the imaging device 142a. As the imaging device 142a, for example, a charge coupled device (CCD) camera, a complementary metal oxide semiconductor (CMOS) camera, can be used. The imaging device drive circuit drives the imaging device 142a under control of the capsule controller 13 to acquire an in-vivo image as an analog signal. The imaging device drive circuit outputs the in-vivo image as an analog signal read from the imaging device 142a to the signal processing unit 143.

The illuminating unit 141 includes, for example, as shown in FIG. 3, a plurality of light sources 141A and a not-shown light source drive circuit for driving each of the light sources 141A. The plurality of light sources 141A are arranged so that light distributions output from the capsule medical apparatus 10 almost coincide by color components. As each of the light sources 141A, for example, a light emitting diode (LED) can be used. The light source drive circuit drives the light sources 141A in accordance with driving of the imaging unit 142 under control of the capsule controller 13 to illuminate the inside of the subject.

The signal processing unit 143 executes predetermined processes such as sampling, amplification, and analog to digital (A/D) conversion on an analog in-vivo image input from the imaging unit 142 to thereby generate a digital in-vivo image. The in-vivo image subjected to the various processes is input to the wireless transmitting unit 15.

The in-vivo information acquiring unit 14 may have a not-shown sensor device and a sensor device drive circuit for driving the sensor device. The sensor device includes, for example, a thermometer, a pressure meter, a pH meter, and the like and properly obtains temperature, pressure, pH value, and the like in the subject as subject in-vivo information. The sensor device drive circuit drives the sensor device to obtain the in-vivo information and supplies it to the wireless transmitting unit 15 under control of the capsule controller 13.

The wireless transmitting unit 15 is connected to the transmitting antenna 15a constructed by a coil antenna or the like, executes various processes such as superposition, modulation, up-conversion, and the like to a transmission reference frequency signal on the in-vivo information such as an in-vivo image input from the signal processing unit 143 and, after that, transmits the resultant signal as a wireless signal from the transmitting antenna 15a to the external device 200. That is, the wireless transmitting unit 15 also functions as an in-vivo information transmitting unit (for example, an image transmitting unit) for transmitting in-vivo information (for example, an in-vivo image) acquired by the in-vivo information acquiring unit 14 (for example, an imaging unit) to the external device 200.

The wireless receiving unit 16 is connected to the receiving antenna 16a constructed by a coil antenna or the like, receives various operation instructions and the like transmitted as wireless signals from the external device 200 via the receiving antenna 16a, executes various processes such as filtering, down-conversion, demodulation, decoding, and the like on the received signals, and outputs the resultant signals to the capsule controller 13.

The capsule controller 13 is constructed by, for example, a central processing unit (CPU), a microprocessor unit (MPU), or the like, and controls the components in the capsule medical apparatus 10 by reading and executing a program and parameters read from a not-shown memory unit on the basis of the various operation instructions and the like input from the external device 200 via the wireless receiving unit 16.

The capsule internal power source 17 includes, for example, a button cell such as a primary cell or secondary cell, a power supply circuit for boosting power output from the button cell and supplying the boosted power to the components in the capsule medical apparatus 10, and the like, and supplies drive power to the components in the capsule medical apparatus 10.

As the magnetic field generator 12, for example, a permanent magnet or the like can be used. However, it is not limited to a permanent magnet but any configuration which is magnetized by a magnetic field input from the outside and makes the capsule medical apparatus 10 generate driving power, rotational force, or the like.

The resonance magnetic field generator 11 includes an LC resonance circuit 111 made by a capacitor (C) and an inductor (L) which are connected in parallel, and emits a resonance magnetic field at a resonance frequency F0 by being excited by a magnetic field (hereinbelow, called "drive magnetic field") having a frequency almost equal to the resonance frequency F0 input from the outside. The resonance frequency F0 is a resonance frequency of the LC resonance circuit 111 determined by the capacitor (C) and the inductor (L) which are connected in parallel.

The above-described components (11, 12, 13, 14, 15, 15a, 16, 16a, and 17) are housed in a capsule-shaped casing 18. As shown in FIG. 3, the casing 18 is made by a container 18a having an almost cylindrical shape or a semi-ellipse spherical shape whose one end has a hemispherical dome shape and whose other end is open, and a cap 18b having a hemispherical shape and, when being fit in the opening in the container 18a, water-tightly sealing the casing 18. The casing 18 has, for example, a size to a degree that it can be swallowed by the subject. In the embodiment, at least the cap 18b is formed of a transparent material. The light sources 141A are mounted on a circuit board 141B on which the above-described light source drive circuit (not shown) is mounted. Similarly, the imaging device 142a and the objective lens 142c are mounted on a circuit board (not shown) on which an imaging device drive circuit is mounted. The circuit board 141B on which the light sources 141A are mounted and the circuit board on which the imaging device 142a is mounted are disposed on the side of the cap 18b in the casing 18. The device mounting face of each of the circuit boards is oriented toward the cap 18b side. Therefore, as shown in FIG. 3, the imaging/illuminating direction of the imaging device 142a and the light sources 141A is oriented to the outside of the capsule medical apparatus 10 via the transparent cap 18b.

Detection Space

Referring again to FIG. 1, the description will be continued. In the detection space K, drive coils 224, 224y, and 224z generating an almost uniform drive magnetic field in the detection space K, a plurality of sense coils 214 for detecting the resonance magnetic field generated by the LC resonance circuit 111 of the capsule medical apparatus 10, and guidance coils 234x, 234y, and 234z for guiding the position and direction (posture) of the capsule medical apparatus 10 are disposed. In the detection space K, a pair of not-shown drive coils or guidance coils opposed to each other so as to sandwich the detection coil K is provided for each of the drive coils 224x to 224z and the guidance coils 234x to 234z. However, in FIG. 1 and in the following description, for simplicity, the opposed coils are not shown, and the shown coils will be mentioned.

The drive coil 224x generates, for example, an almost uniform drive magnetic field made by lines of magnetic force extending in the x axis direction in the detection space K. Similarly, the drive coils 224y and 224z generate, for example, almost uniform drive magnetic fields made by lines of magnetic force extending in the y axis direction and the z axis direction, respectively, in the detection space K. With a configuration that the drive magnetic fields made by different lines of magnetic forces can be generated, regardless of the direction in the detection space K of the LC resonance circuit 111 (particularly, the inductor (L)) in the capsule medical apparatus 10, the resonance magnetic field of stable intensity can be generated in the LC resonance circuit 111. Thus, the position detection precision can be improved.

Each of the sense coils 214 is, for example, a magnetic sensor made by three coils capable of detecting the magnetic field intensities and directions of the three axes (in FIG. 1, x axis, y axis, and z axis). The plurality of sense coils 214 are disposed, for example, in a state where they are arranged two-dimensionally on a plane, in positions where they are not easily influenced by the drive magnetic field and can easily detect the resonance magnetic field generated by the LC resonance circuit 111. In the embodiment, the plurality of sense coils 214 are disposed on the bottom face of the detection space K (the x-y plane at the bottom of the detection space K). The embodiment is not limited to the configuration. Each of the sense coils 214 is not limited to the magnetic sensor made of the coils but can be constructed by a magnetic sensor made by, for example, a magnetoresistive element, a magnetic impedance device (MI device), and the like. Each sense coil 214 can be constructed by a uniaxial magnetic sensor or the like.

The guidance coil 234x generates, for example, an almost uniform guidance magnetic field made by lines of magnetic force extending in the x axis direction in the detection space K. Similarly, the guidance coils 234$y$ and 234$z$ generate, for example, almost uniform guidance magnetic fields made of lines of magnetic force extending in the y axis direction and the z axis direction, respectively, in the detection space K. With a configuration that the drive magnetic fields made by different lines of magnetic forces can be generated, regardless of the direction in the detection space K of the magnetic field generator 12 (permanent magnet) in the capsule medical apparatus 10, the resonance the magnetic field generator 12 and the guidance magnetic field can be stably attracted. Thus, the position and direction of the capsule medical apparatus 10 can be stably guided.

External Device

The external device 200 includes the drive magnetic field generating apparatus 220A for supplying a signal (hereinbelow, called a "drive signal") for generating drive magnetic fields used in a passive mode to the drive coils 224$x$, 224$y$, and 224$z$, a position deriving unit 210 for deriving the position and direction of the capsule medical apparatus 10 from a voltage change (hereinbelow, called a "detection signal") obtained by the sense coil 214, a guidance signal output unit 230 for supplying a signal (hereinbelow, called a "guidance signal") for properly generating a guidance magnetic field that controls the position and direction of the capsule medical apparatus 10 to the guidance coils 234, 234$y$, and 234$z$, a control unit 201 for controlling the components in the external device 200, a memory unit 202 for storing various programs, parameters, and the like which are executed when the control unit 201 controls the components, an operation unit 203 with which the operator enters various operation instructions to the capsule medical apparatus 10, a display unit 204 for displaying the information of the position and direction (hereinbelow, called "position and direction information") of the capsule medical apparatus 10 and in-vivo information obtained from the capsule medical apparatus 10 by an image (including a video image) and sound, a wireless receiving unit 205 and a receiving antenna 205$a$ for receiving in-vivo information and the like transmitted as a wireless signal from the capsule medical apparatus 10, and a wireless transmitting unit 206 and a transmitting antenna 206$a$ for transmitting various operation instructions such as an imaging instruction as wireless signals to the capsule medical apparatus 10.

The control unit 201 is constructed by, for example, a CPU, an MPU, and controls the components in the external device 200 in accordance with a program and parameters read from the memory unit 202. For example, by reading a predetermined program from the memory unit 202 and executing it, the control unit 201 realizes a drive magnetic field generation controller 201A which will be described later. The details of the drive magnetic field generation controller 201A in the embodiment will be mentioned later.

The memory unit 202 is constructed by, for example, a random access memory (RAM), a read only memory (ROM), and the like and holds programs and parameters which are executed when the control unit 201 controls the components. The memory unit 202 properly holds the in-vivo image received from the capsule medical apparatus 10 and the position and direction information of the position, direction, and the like of the capsule medical apparatus 10 derived by the position deriving unit 210.

The operation unit 203 is constructed by, for example, a keyboard, a mouse, a numerical keypad, a joystick, and the like and used by the operator to enter various operation instructions to the capsule medical apparatus 10 such as an imaging instruction (including other in-vivo information acquiring instructions) and various operation instructions to the external device 200 such as a movement instruction at the time of guiding the capsule medical apparatus 10 and a screen switching instruction of switching a screen to be displayed on the display unit 204. The function of switching a screen to be displayed on the display unit 204 may be provided when the capsule medical apparatus 10 includes a plurality of imaging units 142 and images acquired by the capsule medical apparatus 10 are displayed in an almost real-time manner on the display unit 204.

The display unit 204 is a display device such as a liquid crystal display, a plasma display, or an LED array and displays the position and direction information of the capsule medical apparatus 10 and in-vivo information such as an in-vivo image transmitted from the capsule medical apparatus 10. On the display unit 204, a voice reproducing function using a speaker or the like may be mounted. Using the sound reproducing function, the display unit 204 notifies the operator of various operation guidances and information such as a battery remaining amount of the capsule medical apparatus 10 (including a warming) by sound.

The wireless receiving unit 205 is connected to the receiving antenna 205$a$ such as a dipole antenna disposed close to the detection space K, receives an in-vivo image or the like transmitted as a wireless signal from the capsule medical apparatus 10 via the receiving antenna 205$a$, executes various processes such as filtering, down-conversion, demodulation, decoding, and the like on the received signal, and outputs the resultant signal to the control unit 201. That is, the wireless receiving unit 205 also functions as an in-vivo information receiving unit (for example, an image receiving unit) that receives the in-vivo information (for example, an in-vivo image) transmitted from the capsule medical apparatus 10.

The wireless transmitting unit 206 is connected to the transmitting antenna 206$a$ such as a dipole antenna disposed close to the detection space K, executes various processes such as superimposing, modulation, up-conversion, and the like on signals such as various operation instructions to the capsule medical apparatus 10, input from the control unit 201 and, after that, transmits the resultant signal as an electric wave signal from the transmitting antenna 206$a$ to the capsule medical apparatus 10.

The drive magnetic field generating apparatus 220A includes for example, in FIG. 1, a drive signal output unit 220$x$ for making the drive coil 224$x$ generate a magnetic field for driving a line of magnetic force extending in the x axis direction, a drive signal output unit 220$y$ for making the drive coil 224$y$ generate a magnetic field for driving a line of magnetic force extending in the y axis direction, and a drive signal output unit 220$z$ for making the drive coil 224$z$ generate a magnetic field for driving a line of magnetic force extending in the z axis direction. That is, the drive signal output unit 220$x$ and the drive coil 224$x$ function as a drive magnetic field generating unit that generates a magnetic field for driving a line of magnetic force extending in the x axis direction, the drive signal output unit 220$y$ and the drive coil 224$y$ function as a drive magnetic field generating unit that generates a magnetic field for driving a line of magnetic force extending in the y axis direction, and the drive signal output unit 220$z$ and the drive coil 224$z$ function as a drive magnetic field generating unit that generates a magnetic field for driving a line of magnetic force extending in the z axis direction. The invention, however, is not limited to the components but a drive magnetic field generating unit for generating a magnetic field for driving a line of magnetic force which is not parallel to any axis direction may be provided. In the following description, an arbitrary drive signal output unit (the drive signal output unit 220$x$, 220$y$, or 220$z$) will be simply called a drive signal output unit 220.

The drive signal output unit 220x includes a signal generating unit 221x, a drive coil driving unit 222x, and a current detecting unit 223x. Similarly, the drive signal output unit 220y includes a signal generating unit 221y, a drive coil driving unit 222y, and a current detecting unit 223y. The drive signal output unit 220z has the signal generating unit 221y, a drive coil driving unit 222z, and a current detecting unit 223z. That is, the drive magnetic field generating apparatus 220A includes, for the drive coils 224x, 224y, and 224z, the signal generating units 221x, 221y, and 221z, the drive coil driving units 222x, 222y, and 222z, and the current detecting units 223x, 223y, and 223z, respectively. In the following description, reference numerals for arbitrary drive coil 224x, 224y, or 224z, arbitrary signal generating unit 221x, 221y, or 221z, arbitrary drive coil driving unit 222x, 222y, or 222z, and arbitrary current detecting unit 223x, 223y, or 223z will be 224, 221, 222, and 223, respectively.

The signal generating unit 221 calculates a signal waveform having a frequency almost equal to the resonance frequency F0 of the LC resonance circuit 111 in the capsule medical apparatus 10 in accordance with a control signal input from the control unit 201, generates a drive signal having the signal waveform, and outputs the drive signal to the drive coil driving unit 222.

The drive coil driving unit 222 current-amplifies the drive signal input from the signal generating unit 221 and inputs the amplified drive signal to the drive coil 224 via the current detecting unit 223. The drive coil 224 to which the amplified drive signal is input emits a magnetic field having a frequency almost equal to the resonance frequency F0 of the LC resonance circuit 111 in the capsule medical apparatus 10, thereby generating a drive magnetic field which makes the LC resonance circuit 111 excited in the detection space K. The current amplification factor by the drive coil driving unit 222 is set in consideration of the processing capability (such as dynamic range) of the sense coil 214 and a signal processing unit 211 which will be described later, the S/N ratio of a detection signal obtained by the sense coil 214, and the like.

Figure 4:
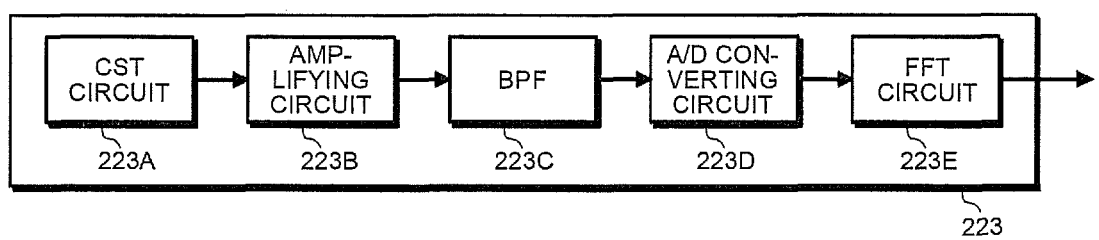
FIG. 4 is a block diagram showing a schematic configuration of a current detecting unit according to the first or second embodiment of the invention.

The current detecting unit 223 includes, as shown in FIG. 4, a current sensing transform (hereinbelow, called "CST") circuit 223A, an amplifying circuit 223B, a band-pass filter (hereinbelow, called "BPF") 223C, an A/D (Analog to Digital, hereinbelow, called "A/D") converting circuit 223D, and a fast Fourier transform (hereinbelow, called "FFT") circuit 223E. FIG. 4 is a block diagram showing a schematic configuration of the current detecting unit 223 according to the embodiment.

Figure 5:
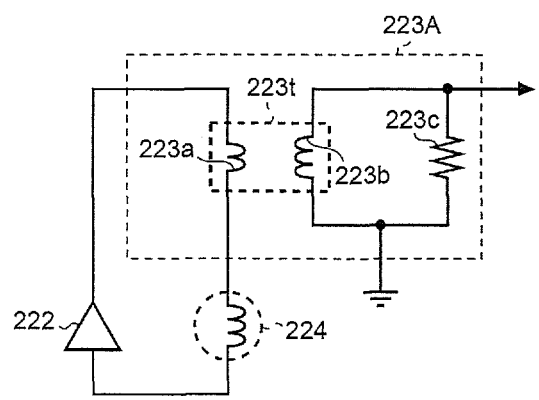
FIG. 5 is an equivalent circuit diagram showing a schematic configuration of a CST circuit according to the first embodiment of the invention.

The CST circuit 223A includes, as shown in FIG. 5, a transform circuit 223t made by a primary coil 223a provided between the drive coil driving unit 222 and the drive coil 224 and a secondary coil 223b disposed opposing to the primary coil 223a, and a load resistor 223c connected in parallel with the secondary coil 223b. Therefore, when the drive signal output from the drive coil driving unit 222 flows in the primary coil 223a, by the drive signal, current flows in the secondary coil 223b. The current after flowing in the secondary coil 223b is output as a signal of detection of a current value of the current to be input to the drive coil 224 (hereinbelow, called a "current detection signal") from the CST circuit 223A. FIG. 5 is an equivalent circuit diagram showing a schematic configuration of the CST circuit 223A according to the embodiment.

The current detection signal output from the CST circuit 223A is amplified by the amplifying circuit 223B, is band-limited by the BPF 223C and, after that, converted from an analog signal to a digital signal in the A/D converting circuit 223D. The digitized current detection signal is input and subjected to fast Fourier transform in the FFT circuit 223E. As a result, the intensity information (information indicative of the magnitude of current, hereinbelow, called "FFT data") of the current detection signal obtained in the CST circuit 223A is acquired. The FFT data output from the FFT circuit 223E is input to the control unit 201. The control unit 201 enters the input FFT data to the drive magnetic field generation controller 201A which will be described later.

Referring again to FIG. 1, description will be continued. The position deriving unit 210 in the external device 200 derives, in an almost real-time manner, the position and direction (position and direction information) of the capsule medical apparatus 10 by executing a predetermined process using information of a magnetic field included in a detection signal detected by the sense coil 214.

The position deriving unit 210 includes, for example, the signal processing unit 211 and a position calculating unit 212. The signal processing unit 211 receives each of the detection signals detected by the plurality of sense coils 214. The signal processing unit 211 properly performs amplification, band limitation, A/D conversion, and FFT on the input detection signals and outputs the processed detection signals (FFT data). The signal processing unit 211 periodically receives the detection signals (FFT data) from the sense coils 214, executes the above-described signal processes on the input signals and, after that, supplies the resultant signals to the position calculating unit 212. The detection signal output from the sense coil 214 is a signal expressing, in voltage, magnetic field information such as intensity and direction of the magnetic field. The band limitation is executed to eliminate a frequency component apart from the resonance frequency F0 by a predetermined bandwidth or more, such as information of the guidance magnetic field (hereinbelow, called "guidance magnetic field information"), information of noise, and the like from the detection signal.

The position calculating unit 212 derives the present position and direction information of the capsule medical apparatus 10 from the magnetic field information included in the detection signal by executing a predetermined arithmetic process on the detection signal entered from the signal processing unit 211. The position calculating unit 212 outputs the derived position and direction information to the control unit 201.

The detection signal input to the position calculating unit 212 includes not only the information of the resonance magnetic field (hereinbelow, called "resonance magnetic field information") emitted from the LC resonance circuit 111 but also information of an unnecessary magnetic field (hereinbelow, called "unnecessary magnetic field") having a frequency almost equal to the resonance frequency F0. As the unnecessary magnetic field, a drive magnetic field for exciting the LC resonance circuit 111 in a passive method and a resonance magnetic field emitted from a coil (such as the guidance coils 234x to 234z and the drive coils 224x to 224z) disposed close to the detection space K is excited by the resonance magnetic field emitted from the LC resonance circuit 111 exist.

In the embodiment, a process for eliminating the unnecessary magnetic field information is executed on the detection signal output from the signal processing unit 211. It enables only the resonance magnetic field information to be extracted from the detection signal, so that high-precision position detection becomes possible.

For example, the process of eliminating the drive magnetic field information from the magnetic field information included in the detection signal output from the signal processing unit 211 (hereinbelow, called "calibration process") is performed as follows. In a state where the capsule medical apparatus 10 (that is, the "LC resonance circuit 111") is not introduced in the detection space K, the drive coils 224x, 224y, and 224z are driven to generate the drive magnetic fields in the detection space K. By driving the signal processing unit 211 and the position calculating unit 212 in this state, magnetic field information including no resonance magnetic field information (hereinbelow, called "calibration information") is derived and held. At the time of position detection, the held calibration information is subtracted from the magnetic field information included in the detection signal by vector operation.

The process of eliminating information of the magnetic field (unnecessary magnetic field information) (hereinbelow, called "correcting process") generated when the drive coils 224x to 224z and/or the guidance coils 234x to 234z are induced by the resonance magnetic field, from the magnetic field information included in the detection signal output from the signal processing unit 211 can be performed as follows. For example, a current detecting unit for detecting current flowing in each of the drive coils 224x to 224z and/or the guidance coils 234x to 234z is provided. From the detected current value, unnecessary magnetic field information of an unnecessary magnetic field generated from each of the coils is calculated and subtracted from the magnetic field information included in the detection signal by vector operation.

The position and direction information output from the position calculating unit 212 is input to the control unit 201. The control unit 201 displays the information such as the present position and direction of the capsule medical apparatus 10 on the display unit 204 by using the input position and direction information. The operator can recognize the present position and direction of the capsule medical apparatus 10 from the display unit 204.

The operator can enter an operation instruction of operating the position and direction of the capsule medical apparatus 10 with the operation unit 203. Further, the operator can also enter an instruction of obtaining in-vivo information to the capsule medical apparatus 10 using the operation unit 203.

The control unit 201 calculates information including a guidance magnetic field (hereinbelow, called "guidance information") to be given to the magnetic field generator (permanent magnet) 12 mounted on the capsule medical apparatus 10 from the present position and direction of the capsule medical apparatus 10 and a target position and direction entered from the operation unit 203, and supplies it to the guidance signal output unit 230.

The guidance signal output unit 230 includes a signal generating unit 231 and a guidance coil driving unit 232. The guidance information calculated by the control unit 201 is input to the signal generating unit 231 in the guidance signal output unit 230. The signal generating unit 231 calculates a signal waveform necessary to generate the guidance magnetic field in accordance with the input guidance information and generates and outputs a guidance signal having the signal waveform.

The guidance signal output from the signal generating unit 231 is input to the guidance coil driving unit 232. The guidance coil driving unit 232 current-amplifies the input guidance signal and, after that, properly supplies the amplified signal to the guidance coils 234x to 234z. A magnetic field is emitted from the guidance coils 234x to 234z properly selected, and a guidance magnetic field for guiding the capsule medical apparatus 10 in the target position and direction is generated in the detection space K. That is, the guidance signal output unit 230 and the guidance coil 224 function as a capsule guiding unit for guiding the capsule medical apparatus 10 in a target position and direction.

Drive Magnetic Field Generation Controller

Figure 6:
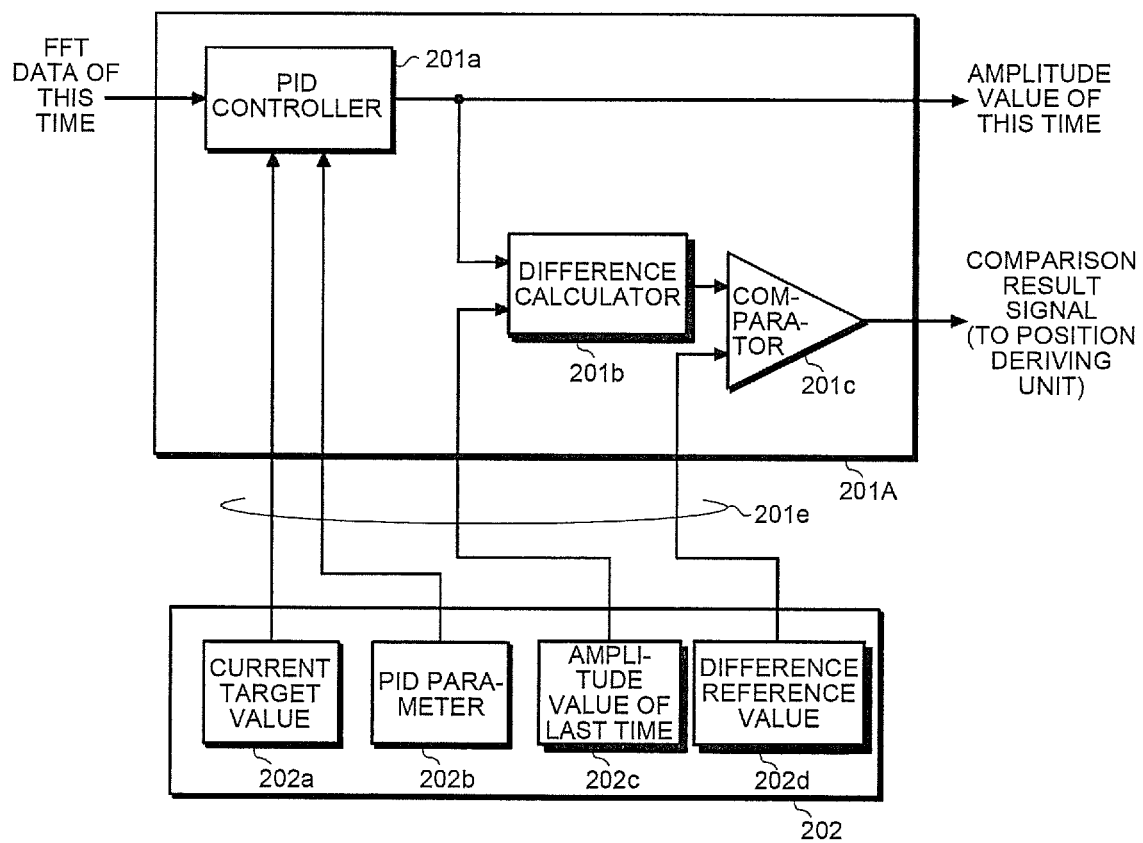
FIG. 6 is a functional block diagram showing a schematic configuration of a drive magnetic field generation controller realized in a control unit according to the first or second embodiment of the invention.

Next, the drive magnetic field generation controller 201A for generating a stable drive magnetic field by feedback-controlling each of the drive signal output units 220 in the drive magnetic field generating apparatus 220A will be described in detail with reference to the drawings. FIG. 6 is a functional block diagram showing a schematic configuration of the drive magnetic field generation controller 201A realized in the control unit 201 according to the embodiment.

As shown in FIG. 6, the drive magnetic field generation controller 201A includes a PID controller 201a, a difference calculator 201b, and a comparator 201c. To the drive magnetic field generation controller 201A, the latest FFT data (hereinbelow, called "FFT data of this time") calculated in the current detecting unit 223 in each drive signal output unit 220 is sequentially entered. A current target value 202a, a PID parameter 202b, an amplitude value 202c of last time, and a difference reference value 202d are held in the memory unit 202, and are referred to by the drive magnetic field generation controller 201A (that is, the control unit 201) via a bus 201e or the like. As described above, the memory unit 202 functions as a last-time amplitude value storing unit for storing an amplitude value of a drive signal output last time (amplitude value of last time) from the drive magnetic field generation controller 201A to the signal generating unit 221, and also functions as a difference reference value storing unit for storing a reference value (difference reference value) with respect to the difference between the amplitude value of last time stored in the last-time amplitude value storing unit and an amplitude value (new amplitude value) newly calculated by the drive magnetic field generation controller 201A.

The PID controller 201a receives FFT data of this time output from the current detecting unit 223, reads the current target value 202a held in the memory unit 202, and calculates an error, an accumulated error, and an error change rate of the FFT data of this time which is input with respect to the read current target value 202a. The current target value is a target value of the current amplitude of the drive signal input to the drive coil 224 and is a value scaled in accordance with a processing system obtained by the fast Fourier transform (FFT). Therefore, the drive magnetic field generation controller 201A feedback-controls each of the drive signal output units 220 so that the current value detected by the current detecting unit 223 becomes close to the current target value 202a.

The PID controller 201a reads the PID parameter 202b from the memory unit 202 and calculates and outputs an amplitude value of a drive signal (hereinbelow, called a "new amplitude value") generated by the signal generating unit 221 in each of the drive signal output units 220 by using the calculated error, the accumulated error, the error change rate, and the read PID parameter 202b. The PID parameter is a parameter for calculating the new amplitude value of the drive signal from the error, the accumulated error, and the error change rate on the basis of the PID control.

The new amplitude value output from the PID controller 201a is supplied to each of the difference calculator 201b and a selector 201d. The difference calculator 201b reads the amplitude value 202c of last time (hereinbelow, called "a last-time amplitude value") from the memory unit 202, and calculates the difference between the read amplitude value and a new amplitude value. The difference calculator 201b outputs the calculated difference to the comparator 201c.

To the comparator 201c, except for the difference output from the difference calculator 201b, the difference reference value 202d read from the memory unit 202 is supplied. The difference reference value is a preset value for the difference output from the difference calculator 201b and is a reference value for determining whether an amplitude value largely changes from an amplitude value of last time. The comparator 201c outputs a result of comparison between the input difference and the read difference reference value 202d as a comparison result signal indicative of the degree of stability of the drive magnetic field. For example, when the absolute value of the difference input from the difference calculator 201b is larger than the difference reference value 202d, the comparator 201c outputs, for example, a comparison result signal of the high level. When the absolute value of the difference is equal to or less than the difference reference value 202d, for example, the comparator 201c outputs a comparison result signal of the low level.

The comparison result signal output from the comparator 201c is input to the position deriving unit 210 via the control unit 201. When the comparison result signal indicates that the absolute value of the difference between the amplitude value of last time and the new amplitude value is larger than the difference reference value 202d (for example, the comparison result signal is at the high level), for example, the position deriving unit 210 does not execute the position deriving process or invalidates the detection signal (FFT data) output from the signal processing unit 211 or the position and direction information derived in the position calculating unit 212. It can avoid derivation of the position and direction information at a timing when there is the possibility that position detection precision deteriorates, and the position detecting magnetic guidance system 1 capable of detecting a position with improved precision can be realized. When the comparison result signal indicates that the absolute value of the difference between the amplitude value of last time and the new amplitude value is equal to or less than the difference reference value 202d (for example, the comparison result signal is at the low level), the position deriving unit 210 validates the detection signal (FFT data) output from the signal processing unit 211, executes the position deriving process, and processes position and direction information derived by the process as valid information.

To prevent that the position and direction information at a timing (interval) when the position and direction information is not derived or the derived position and direction information is invalidated becomes blank (null), position and direction information calculated at the timing of last time may be inserted as position and direction information at the timing (interval). The inserting process may be executed by, for example, the control unit 201 or the position calculating unit 212 in the position deriving unit 210.

Figure 7:
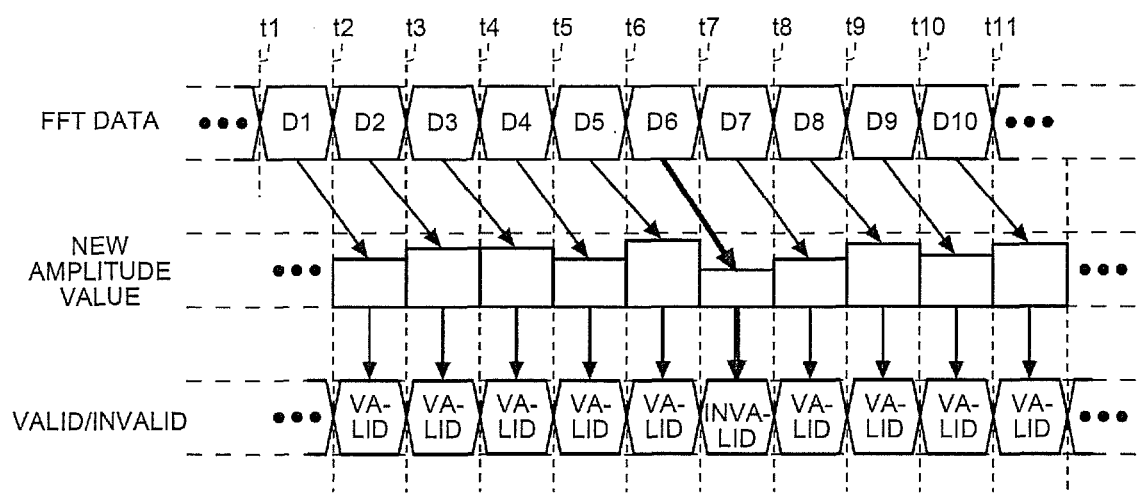
FIG. 7 is a timing chart for explaining outline of PID control according to the first embodiment of the invention.

Outline of PID control in the embodiment will now be described. FIG. 7 is a timing chart for explaining outline of PID control according to the embodiment. It is understood from FIG. 7 that, for example, when the FFT circuit 223E generates FFT data D1 at a timing t1, at a timing t2 as the next timing, the drive magnetic field generation controller 201A performs the PID process or the like using the FFT data D1, thereby executing calculation of a new amplitude value and specification of an amplitude value used as an amplitude value of this time. Hereinafter, operations are performed similarly also at timings t2 to t11.

In the embodiment, for example, as shown in FIG. 7, when a new amplitude value generated at timing t7 is invalidated, as described above, the drive magnetic field generation controller 201A uses the amplitude value used at the timing t6 as the timing of last time (the amplitude value 202c of last time). Consequently, a control signal for making the signal generating unit 221 generate a drive signal can be prevented from becoming blank (null), and an amplitude value which does not cause a sharp amplitude change can be specified easily.

As described above, in the embodiment, the current value of the drive signal output from the signal generating unit 221 and subjected to amplitude amplification in the drive coil driving unit 222 is detected by the current detecting unit 223. The drive magnetic field generation controller 201A feedback-controls the signal generating unit 221 in accordance with the detected current value so that a drive signal generated by the signal generating unit 221 becomes close to a current target value. When the amplitude value changes largely from that of last time, the drive magnetic field generation controller 201A invalidates the amplitude value of this time and uses the amplitude value of last time. Therefore, the signal generating unit 221 can be made generate a drive signal having a stable amplitude around the current target value.

First Modification

The position detecting magnetic guidance system 1 according to the embodiment can be variously modified to derive more accurate position and direction information as follows. An average value of detection signals (FFT data) output from the signal processing unit 211 of the position deriving unit 210 is obtained and, using the averaged detection signal (FFT data), the position calculating unit 212 calculates position and direction information, or the position and direction information output from the position deriving unit 210 is averaged by the control unit 201. In the following, the case of averaging the detection signals (FFT data) will be described as a first modification of the embodiment. In the following description, the detection signal (FFT data) will be simply called FFT data.

Figure 8:
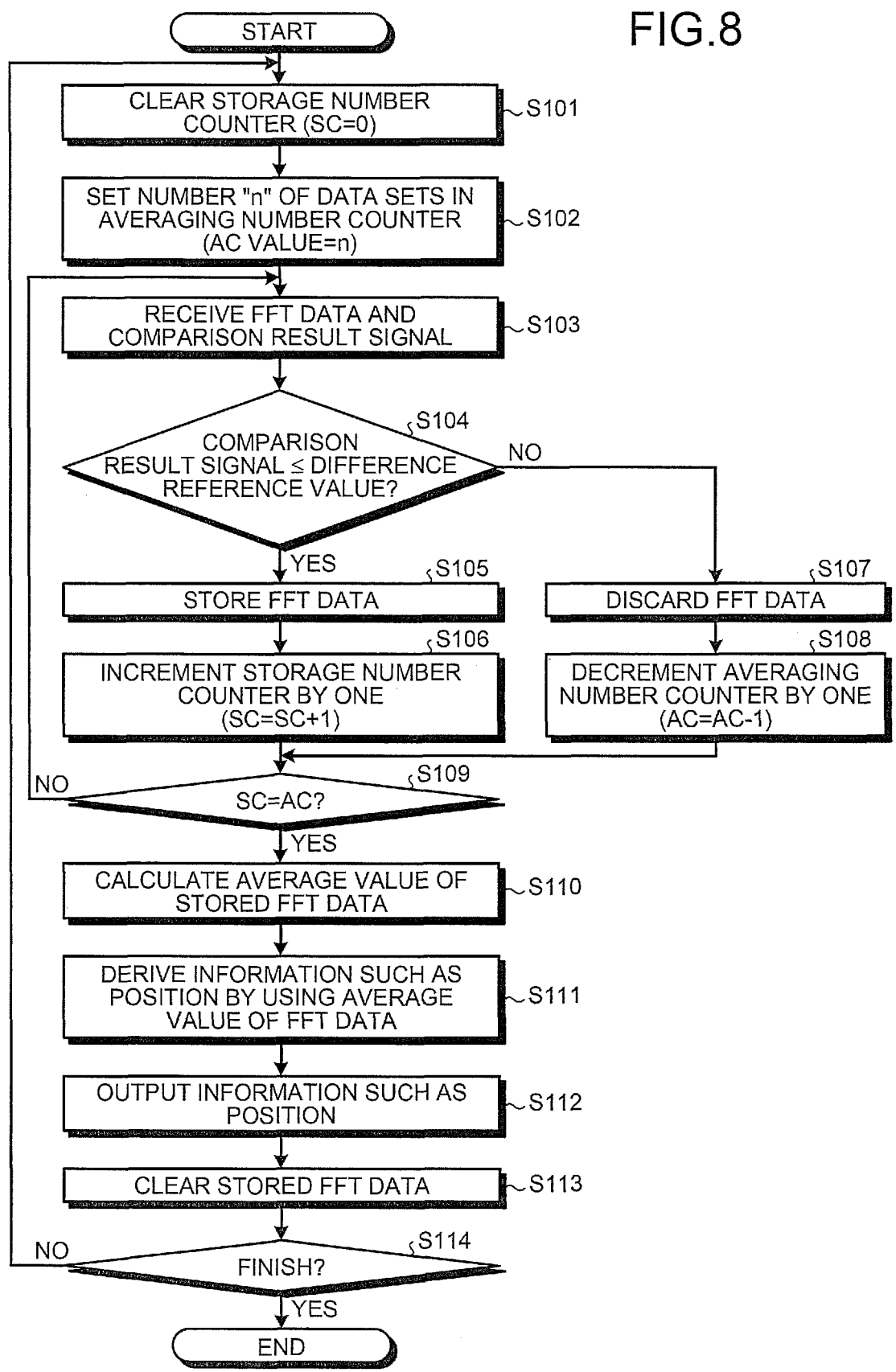
FIG. 8 is a flowchart showing schematic operations of a position calculating unit according to a first modification of the first embodiment of the invention.

FIG. 8 is a flowchart showing schematic operations of the position calculating unit 212 in the first modification. In the first modification, the position calculating unit 212 has an up counter (hereinbelow, called a "storage number counter") for counting the number of pieces of FFT data stored in the memory unit 202 and a down counter (hereinbelow, called an "average value counter") for managing the number of pieces of FFT data to be averaged.

As shown in FIG. 8, after start, the position calculating unit 212, first, clears the storage number counter (SC=0) (step S101) and, further, sets the number "n" (n: an integer of two or larger) of pieces of data averaged which is preliminarily determined in the averaging number counter (AC=n) (step S102).

Next, the position calculating unit 212 receives FFT data from the signal processing unit 211 and also a comparison result signal output from the control unit 201 (step S103). Subsequently, the position calculating unit 212 determines whether the input comparison result signal indicates that "the absolute value of the difference between the amplitude value of last time and a new amplitude value is equal to or less than the difference reference value 202d" (step S104).

When, as a result of determination in step S104, the comparison result signal indicates that the absolute value is equal to or less than the difference reference value 202d (Yes in step S104), the position calculating unit 212 stores the FFT data received in step S103 into the memory unit 202 or the like (step S105), increments the storage number counter by one (SC=SC+1) (step S106) and moves to step S109.

On the other hand, when, as a result of determination in step S104, the comparison result signal indicates that the absolute value is larger than the difference reference value 202d (No in step S104), the position calculating unit 212 discards the FFT data received in step S103 (step S107), decrements the averaging number counter by one (step S108)

and moves to step S109. As described above, the position calculating unit 212 also functions as a unit of increasing/decreasing the number of data averaged, which substantially decreasing the number "n" of data sets (first predetermined number of times) by decrementing the counter value AC of the averaging number counter by one on the basis of the input comparison result signal, thereby enabling the period of deriving the position and direction information to be maintained constant.

In step S109, the position calculating unit 212 acquires the counter value SC of the storage number counter and the counter value AC of the averaging number counter and determines whether the counter values match (SC=AC?) (step S109). When the counter values do not match (No in step S109), the position calculating unit 212 returns to step S103. On the other hand, when the counter values match (Yes in step S109), the position calculating unit 212 reads the FFT data stored in the memory unit 202, calculates an average value of the FFT data (step S110) and, using the calculated average value of the FFT data, derives the position and direction information of the capsule medical apparatus 10 (LC resonance circuit) (step S111).

Next, the position calculating unit 212 outputs the derived position and direction information to the control unit 201 (step S112) and clears the FFT data stored in the memory unit 202 (step S113). After that, the position calculating unit 212 determines, for example, whether an end instruction is input from the control unit 201 (step S114). When an end instruction is input (Yes in step S114), the position calculating unit 212 finishes the process. On the other hand, when an end instruction is not input (No in step S114), the position calculating unit 212 returns to step S101 and executes similar operations.

Second Modification

The number "n" of data sets in the first modification of the embodiment can be made small, for example, when the position detection is executed stably. When each of the FFT data pieces (or the position and direction information) is accurate, without averaging the larger number of FFT data pieces (or the position and direction information), accurate position and direction information can be obtained.

Further, the number "n" of data sets can be made large, for example, when the position detection is not stable. By obtaining an average value of the larger number of FFT data pieces (or the position and direction information), precision of the derived position and direction information is improved.

The state where the position detection is executed stably denotes a state where the absolute value of the difference between the amplitude value of last time and the new amplitude value is equal to or less than the difference reference value 202d for a relatively long period. The state where the position detection is unstable denotes a state where the absolute value of the difference between the amplitude value of last time and the new amplitude value is equal to or less than the difference reference value 202d for a relatively short period.

Figure 9:
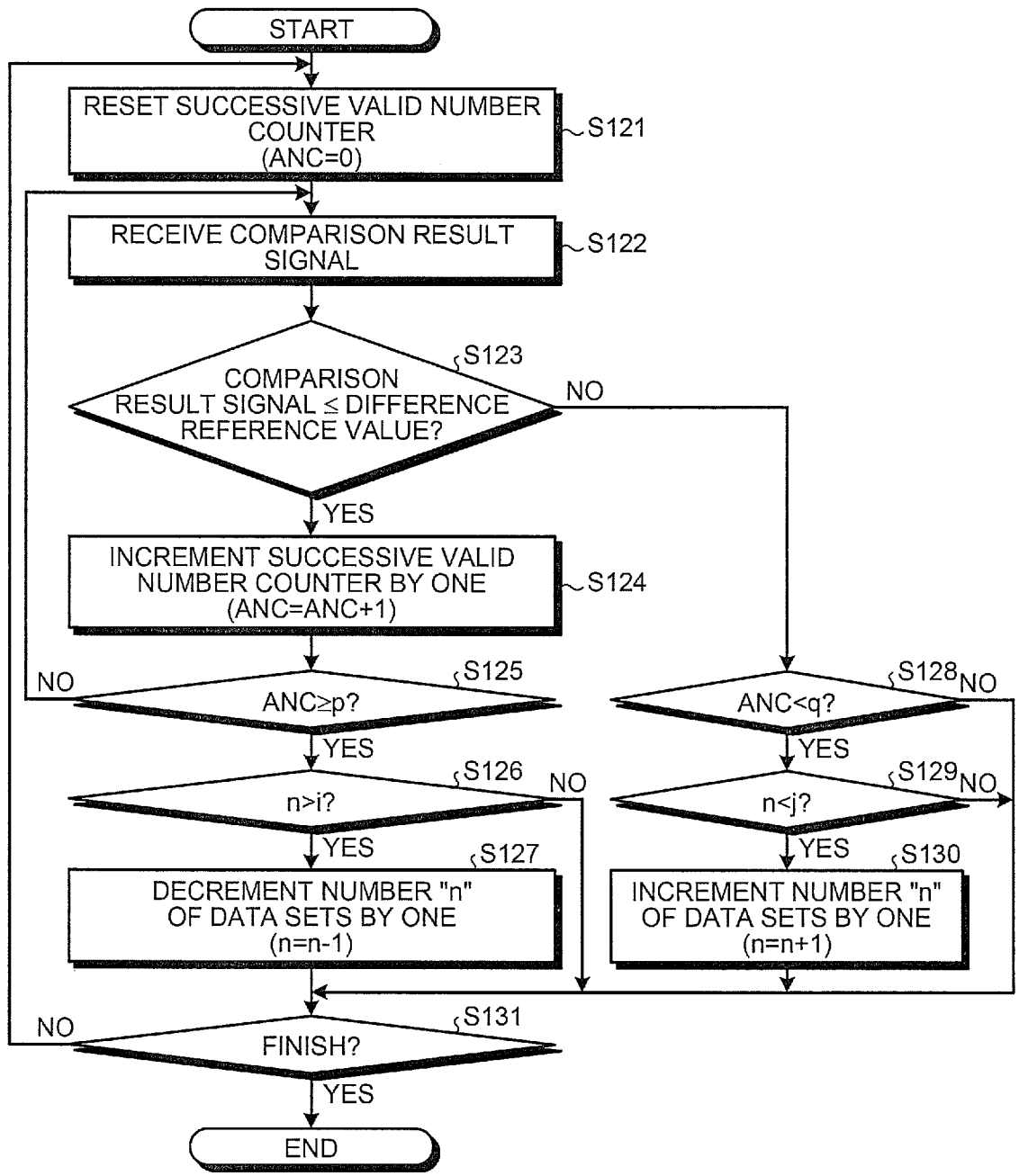
FIG. 9 is a flowchart showing schematic operations performed when the position calculating unit increases/decreases the number of data sets in a second modification of the first embodiment of the invention.

In the second modification, the number of times that the comparison result signal continuously indicates that "the absolute value of the difference between the amplitude value of last time and the new amplitude value is equal to or less than the difference reference value 202d" is counted. When the number of times becomes equal to or larger than the prescribed number "p" of times, the position calculating unit 212 decreases the number "n" of data sets. When the number of times is less than the prescribed number "p", the position calculating unit 212 increases the number "n" of data sets. In the following, the operation will be described in detail with reference to FIG. 9. FIG. 9 is a flowchart showing schematic operations performed when the position calculating unit 212 increases/decreases the number "n" of data sets in the second modification. In the second modification, the position calculating unit 212 has a counter for counting the number of successive times (hereinbelow, called a "successive valid number counter") that "the absolute value of the difference between the amplitude value of last time and the new amplitude value is equal to or less than the difference reference value 202d".

As shown in FIG. 9, after start, first, the position calculating unit 212 clears the successive valid number counter (ANC=0) (step S121). Next, the position calculating unit 212 receives a comparison result signal output from the control unit 201 (step S122), and determines whether the received comparison result signal indicates that "the absolute value of the difference between the amplitude value of last time and the new amplitude value is equal to or less than the difference reference value 202d" (step S123).

When comparison result signal indicates that the absolute value is equal to or less than the difference reference value 202d as a result of determination in step S123 (Yes in step S123), the position calculating unit 212 increments the successive valid number counter by one (ANC=ANC+1) (step S124). Subsequently, the position calculating unit 212 determines whether the counter value ANC of the successive valid number counter is equal to or larger than a predetermined value "p" (p denotes an integer of three or larger, which is larger than "p" which will be described) (step S125). The predetermined value "p" is a value indicating a determination reference for determining that position detection is stable when the comparison result signal indicating that "the absolute value of the difference between the amplitude value of last time and the new amplitude value is equal to or less than the difference reference value 202d" continues by p times or more.

When the counter value ANC is not equal to or larger than the predetermined value "p" as a result of the determination in step S125 (No in step S125), the position calculating unit 212 returns to step S122. On the other hand, when the count value ANC is equal to or larger than the predetermined value "p" as a result of the determination in step S125 (Yes in step S125), the position calculating unit 212 determines whether the present number "n" of data sets managed in the memory unit 202 or the like is larger than a preset lower limit value "i" (i denotes a positive integer) (step S126). When "n" is larger than "i" (Yes in step S126), the position calculating unit 212 decrements the number "n" of data sets by one (step S127) and moves to step S131. In such a manner, the position calculating unit 212 also functions as the unit of increasing/decreasing the number of data to be averaged, which decreases the number "n" of data sets (first predetermined number) on the basis of a comparison result signal received.

On the other hand, as a result of the determination in step S126, when "n" is equal to or less than "i" (No in step S126), the position calculating unit 212 determines that the number "n" of data sets cannot be decremented any more and moves to step S131. The lower limit value "i" is the lower limit value of the number "n" of data sets.

When the comparison result signal is larger than the difference reference value 202d as a result of the determination in step S123 (No in step S123), the position calculating unit 212 determines whether the counter value of the successive valid number counter is smaller than a predetermined value "q" (q is an integer of two or larger) (ANC<q) (step S128). The predetermined value "q" is a value indicative of a determination reference for determining that position detection is not stable when the number of successive times of the comparison result signal indicating that "the absolute value of the difference between the amplitude value of last time and the new amplitude value is equal to or less than the difference reference value $202d$" is equal to or less than "q" times.

When the counter value ANC is equal to or larger than the predetermined value "q" as a result of the determination in step S128 (No in step S128), the position calculating unit 212 moves to step S131. On the other hand, when the counter value ANC is smaller than the predetermined value "q" (third predetermined number of times) as a result of the determination in step S128 (Yes in step S128), the position calculating unit 212 determines that whether the number "n" of data sets at present managed in the memory unit 202 or the like is smaller than the upper limit value "j" ("j" is a positive integer and larger than the above-described "i") (step S129). When "n" is smaller than "j" (Yes in step S129), the position calculating unit 212 increments the number "n" of data sets by one (step S130) and moves to step S131. In such a manner, the position calculating unit 212 also functions as a unit of increasing/decreasing the number of data to be averaged, which increases the number "n" of data sets on the basis of the input comparison result signal.

On the other hand, when "n" is equal to or larger than "j" (No in step S129) as a result of the determination in step S129, the position calculating unit 212 determines that the number "n" of data sets cannot be incremented any more and moves to step S131. The upper limit value "j" is the upper limit value of the number "n" of data sets.

In step S131, the position calculating unit 212 determines, for example, whether an end instruction from the control unit 201 is received. When the end instruction is received (Yes in step S131), the process is finished. On the other hand, when the end instruction is not received (No in step S131), the position calculating unit 212 returns to step S121 and executes similar operations.

Third Modification

In the foregoing embodiments (including the modifications), for example, when the precision of position detection is high, in other words, when the position detection is stable (that is, when the comparison result signal indicating that "the absolute value of the difference between the amplitude value of last time and the new amplitude value is equal to or less than the difference reference value $202d$" continues), the guidance signal output unit 230 is controlled to generate a guidance magnetic field for guiding the capsule medical apparatus 10.

At the time of guiding the capsule medical apparatus 10, a strong guidance magnetic field is generated by using a current larger than that of, for example, the drive magnetic field, so that a noise component included in the guidance magnetic field tends to be large. Consequently, when many frequency components almost equal to the resonance frequency F0 of the LC resonance circuit 111 are included in the noise, there is the case where the precision of the derived position and direction information deteriorates.

Figure 10:
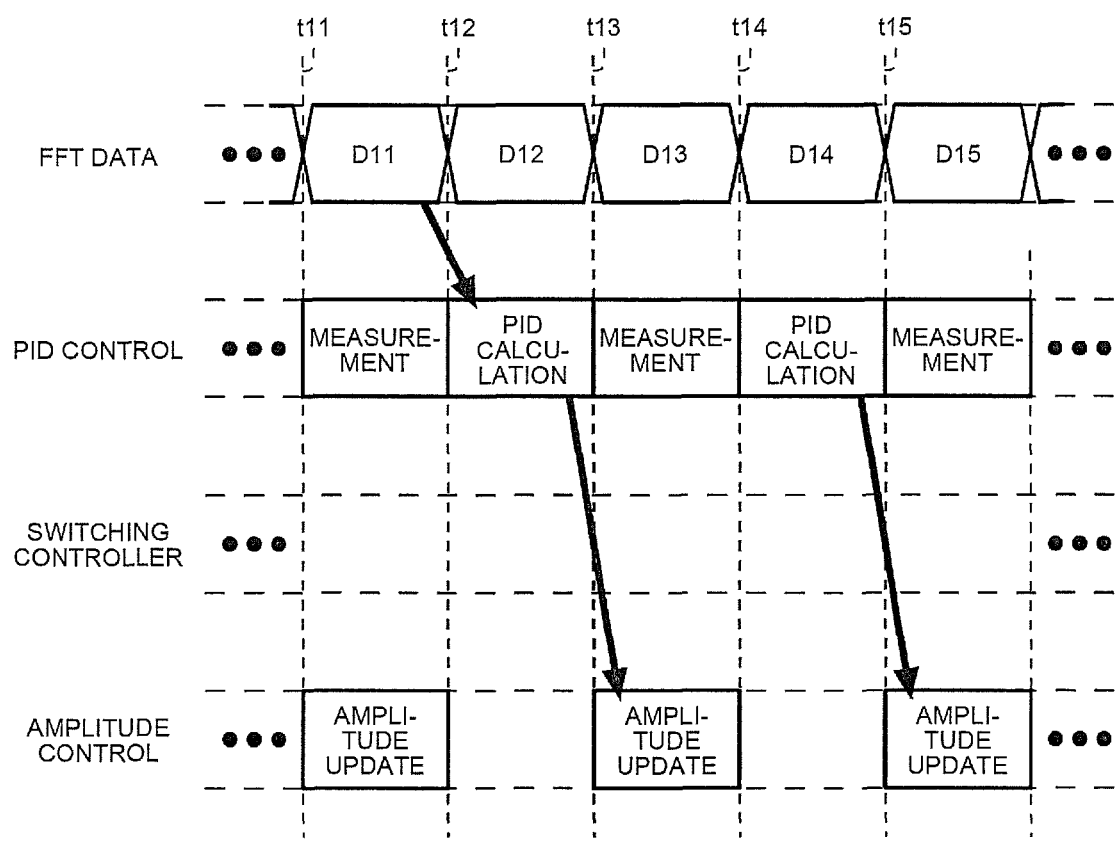
FIG. 10 is a timing chart showing outline of the PID control and amplification control in a third modification of the first embodiment of the invention.

Therefore, as a third modification of the embodiment, for example, when the precision of position detection deteriorates, in other words, when the position detection is not stable (that is, the number of successive times of the comparison result signal indicating that "the difference between the amplitude value of last time and the new amplitude value" is equal to or less than the difference reference value $202d$" is relatively small), the guidance signal output unit 230 may be controlled to generate a guidance magnetic field for guiding the capsule medical apparatus 10. With the configuration, deterioration in the precision of the position detection in a period in which no guidance magnetic field is generated can be avoided. Although the degree of stability in position detection is determined by using the amplitude value of last time and the new amplitude value, the invention is not limited to the configuration. For example, an interval in which the amplitude is not updated such as the interval between timings t12 and t13 and the interval between timings t14 and t15 shown in FIG. 10 may be regarded as an "interval in which position detection is stable", and the guidance magnetic field may be generated in the interval. With the configuration, the influence of noise from the guidance signal output unit 230 and/or the guidance coil 234 can be reduced at the time of measurement of the PID. FIG. 10 is a timing chart showing outline of the PID control and amplification control in the third modification.

Fourth Modification

Figure 11:
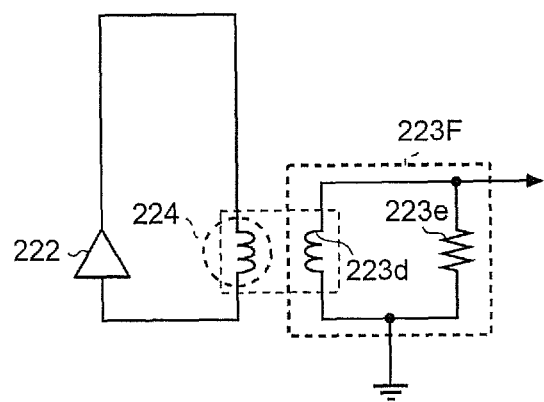
FIG. 11 is an equivalent circuit diagram showing a schematic configuration of a sense coil in a fourth modification of the first embodiment of the invention.

In the foregoing embodiments (including the modifications), current flowing in the drive coil 224 is detected by using the CST circuit 223A. The invention, however, is not limited to the case. For example, as shown in FIG. 11, the drive magnetic field emitted from the drive coil 224 may be directly detected by using a sense coil 223F disposed close to the drive coil 224 in place of the CST circuit 223A. FIG. 11 is an equivalent circuit diagram showing a schematic configuration of the sense coil 223F according to a fourth modification. As shown in FIG. 11, the sense coil 223F includes, for example, a coil $223d$ disposed close to the drive coil 224 and a load resistor $223e$ connected in parallel to the coil $223d$.

With such a configuration, in the fourth modification, the sense coil 223F functions as a secondary coil using the drive coil 224 as a primary coil. Consequently, a configuration similar to, for example, that of the current detecting unit 223 as shown in FIG. 4 can be used.

Fifth Modification

Figure 12:
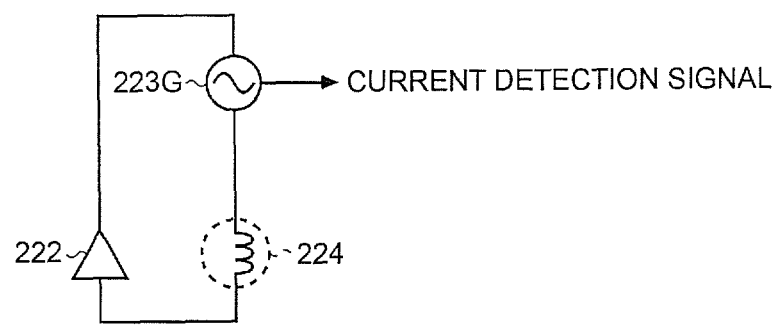
FIG. 12 is a diagram showing connection relations among a drive coil, a drive coil driving unit, and an ammeter in a fifth modification of the first embodiment of the invention.

Further, in place of the CST circuit 223A according to the embodiment or the sense coil 223F according to the fourth modification, for example, as shown in FIG. 12, a line connecting the drive coil 224 and the drive coil driving unit 222 may be provided with an ammeter 223G for measuring current flowing in the line. FIG. 12 is a diagram showing connection relations among the drive coil 224, the drive coil driving unit 222, and the ammeter 223G in the fifth modification.

The ammeter 223G according to the fifth modification outputs the current value of the drive signal input to the drive coil 224 as, for example, a signal of a voltage change (current detection signal) like the CST circuit 223A or the sense coil 223F, so that it can use a configuration similar to, for example, the current detecting unit 223 as shown in FIG. 4.

Second Embodiment

Next, the configuration and operation of a position detecting magnetic guidance system 2 according to a second embodiment of the present invention will be described in detail with reference to the drawings. The same reference numerals are designated to components similar to those of the position detecting magnetic guidance system 1 according to the first embodiment of the invention, and their detailed description will not be repeated.

Figure 13:
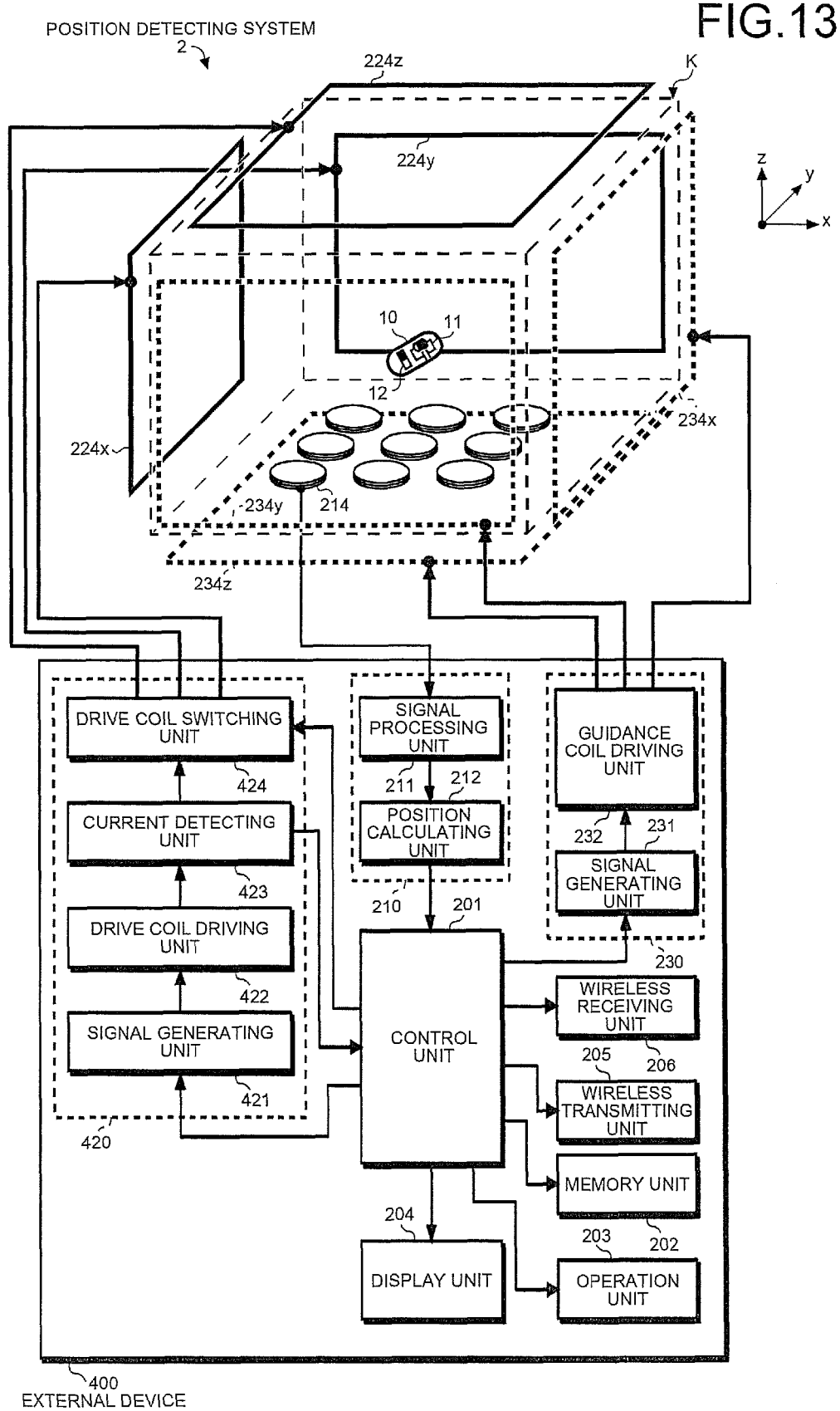
FIG. 13 is a schematic diagram showing a schematic configuration of a position detecting magnetic guidance system according to a second embodiment of the invention.

FIG. 13 is a schematic diagram showing a schematic configuration of the position detecting magnetic guidance system 2 according to the second embodiment. As obvious from comparison between FIGS. 13 and 1, the position detecting magnetic guidance system 2 is different from the position detecting magnetic guidance system 1 with respect to the point that the drive magnetic field generating apparatus 220A is replaced with a drive magnetic field generating apparatus 420.

The drive magnetic field generating apparatus 420 has a signal generating unit 421, a drive coil driving unit 422, a current detecting unit 423, and a drive coil switching unit 424. The signal generating unit 421, the drive coil driving unit 422, and the current detecting unit 423 have similar configurations as those of the signal generating unit 221, the drive coil driving unit 222, and the current detecting unit 223 in the position detecting magnetic guidance system 1, so that detailed description will not be repeated here.

The drive coil switching unit 424 functions as a switch for switching the drive coil 224 connected to the drive coil driving unit 422 via the current detecting unit 423 from any of the drive coils 224x, 224y, and 224z. That is, the drive magnetic field generating apparatus 420 in the embodiment includes the signal generating unit 421, the drive coil driving unit 422, and the current detecting unit 423 commonly used by the plurality of drive coils 224, and a driving coil to which those units are connected is properly switched by using the drive coil switching unit 424.

The switching control of the drive coil switching unit 424 is performed by, for example, a control signal output from the control unit 201. The control unit 201 specifies the drive coil 224 for generating optimum drive magnetic field on the basis of the latest position and direction information of the capsule medical apparatus 10, and controls the drive coil switching unit 424 so that the specified drive coil 424 and the drive coil driving unit 422 are connected to each other.

Figure 14:
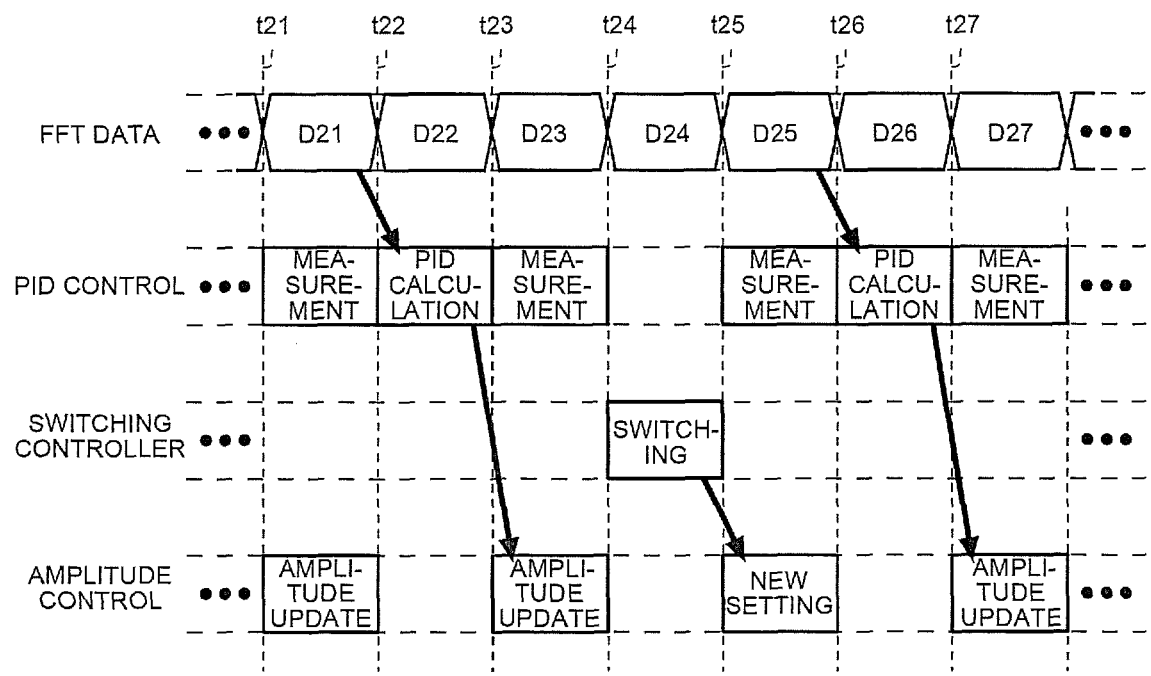
FIG. 14 is a timing chart showing outline of the PID control, switching control, and amplifying control in the second embodiment of the invention.

Preferably, the switching control on the drive coil switching unit 424 by the control unit 201 is executed synchronously with a timing when the position detection precision decreases. The timing of switching control by the embodiment will now be described with reference to FIG. 14. FIG. 14 is a timing chart showing outline of the PID control, switching control, and amplifying control in the second embodiment.

As shown in FIG. 14, for example, in the interval between timings t24 and t25 after the interval between the timings t23 and t24 in which amplitude updating is performed, the amplitude of a drive signal input to the drive coil 224 being selected is switched. There is consequently the possibility that the position detection precision deteriorates. Consequently, by controlling the drive coil switching unit 424 in the interval (t24 to t25), the drive coil 224 being selected is switched. In such a manner, while suppressing the influence on the position detection precision, the drive coil 224 to be used can be switched.

Although FIG. 14 shows the case where the timing of amplitude updating is delayed from the timing of PID calculation by one in order to clarify the timings of controls and the like, the invention is not limited to the case. The timing of the PID calculation and that of the amplitude updating may be the same timing. Although the case of switching the drive coil 224 to be driven and, after that, driving the newly selected drive coil 224 from the next timing is shown as an example in FIG. 14, the invention is not limited to the case. For example, after invalidating FFT data (for example, FFT data D25 or the like) until the drive magnetic field emitted from the newly selected drive coil 224 is stabilized, the PID control and the like may be started.

As described above, when the control unit 201 functions as a switching controller of controlling the drive coil switching unit 424 to switch the drive coil 224 to which the drive coil driving unit 422 is electrically connected to any of the plurality of drive coils (224x to 224z), only the drive coil 224 for generating the drive magnetic field optimum for position detection can be driven. Therefore, power consumption of an external device 400 can be suppressed.

When the degree of stability of the drive magnetic field detected by the drive magnetic field generation controller 201A is low, that is, when the comparison result signal expresses that "the absolute value of the difference between the amplitude value of last time and the new amplitude value is larger than the difference reference value 202d", the control unit 201 controls the drive coil switching unit 424 to switch the drive coil 224 to which the drive coil driving unit 422 is electrically connected to any of the plurality of drive coils (224x to 224z), thereby enabling the influence of the switching control exerted on the position detection precision can be suppressed.

Further, in the embodiment, preferably, the drive coil switching unit 424 electrically disconnects the drive coils 224 which are not driven from the drive coil driving unit 422. With the configuration, the number of coils existing in a valid state close to the detection space K at the time of detection can be decreased. Thus, the number of unnecessary coils exerting an influence on detection of the sense coil 214 can be reduced.

Since the other configuration, operation, and effect are similar to those of the first embodiment of the invention and its modifications, their detailed description will not be given here.

As described above, according to the embodiments of the invention, the degree of stability of the drive magnetic field generated by the drive coil is detected and the amplitude of a drive signal output from the drive coil driving unit can be feedback-controlled in accordance with the degree of stability. Thus, the position detecting system and the method of position detection capable of stably performing accurate position detection by using feedback control can be realized.

The above and other features, advantages and technical and industrial significance of this invention will be better understood by reading the following detailed description of presently preferred embodiments of the invention, when considered in connection with the accompanying drawings.

What is claimed is:

1. A position detecting system comprising:
  a body-insertable apparatus disposed in a state where it is introduced in a subject in a detection space; and
  an external device disposed on the outside of the subject, wherein
  the body-insertable apparatus includes a resonance circuit for emitting a resonance magnetic field by being induced by a drive magnetic field received from the outside, and
  the external device includes:
    a drive coil driving circuit configured to output a drive signal having a predetermined frequency;
    a drive coil configured to receive the drive signal and to generate the drive magnetic field in the detection space based on the drive signal;
    a sense coil configured to detect the resonance magnetic field and to output a detection signal;
    a position deriving circuit configured to derive position information of the resonance circuit by using the detection signal;
    a current detecting circuit configured to detect a current amplitude value of the drive signal input to the drive coil; and
    a drive magnetic field generation control circuit configured to
      calculate an amplitude value of a drive signal which is to be output by the drive coil driving circuit based on the current amplitude value,
      detect a degree of stability of the drive magnetic field on the basis of whether a sharp change occurs in the calculated amplitude value, and control the position deriving circuit to derive position information on the basis of the detected degree of stability of the drive magnetic field.

2. The position detecting system according to claim 1, wherein:
the drive magnetic field generation control circuit is configured to detect the degree of stability of the drive magnetic field by
calculating a difference between a previously calculated amplitude value and a currently calculated amplitude value,
comparing the difference with a preset reference value, and
outputting a result of the comparison as a comparison result signal indicative of the degree of stability to the position deriving circuit, and
the position deriving circuit is further configured to validate or invalidate the detection signal received from the sense coil or the derived position information on the basis of the comparison result signal.

3. The position detecting system according to claim 2, wherein the position deriving circuit is configured to invalidate the detection signal received from the sense coil or the derived position information when the input comparison result signal indicates that the difference is larger than the reference value.

4. The position detecting system according to claim 2, wherein the position deriving circuit includes:
a position calculating unit configured to derive the position information on the basis of an average value of a first predetermined number of times of the detection signals received from the sense coil; and
an average number increasing/decreasing unit configured to increase/decrease the first predetermined number of times on the basis of the input comparison result signal.

5. The position detecting system according to claim 4, wherein the average number increasing/decreasing unit is configured to decrease the first predetermined number of times when the comparison result signal indicating that the difference is equal to or less than the reference value is input to the position deriving circuit successively by a second predetermined number of times or more.

6. The position detecting system according to claim 4, wherein the average number increasing/decreasing unit is configured to increase the first predetermined number of times when the comparison result signal indicating that the difference is larger than the reference value is not input successively by a third predetermined number of times or more.

7. The position detecting system according to claim 5, wherein the average number increasing/decreasing unit is configured to increase the first predetermined number of times when the comparison result signal indicating that the difference is larger than the reference value is not input successively by a third predetermined number of times or more.

8. The position detecting system according to claim 1, wherein the external device includes:
a plurality of the drive coil;
a drive coil switching circuit configured to switch a drive coil to which the drive coil driving circuit is electrically connected to any of the plurality of drive coils; and
a switching controller configured to control the drive coil switching circuit to switch a drive coil to which the drive coil driving circuit is electrically connected to any of the plurality of drive coils, wherein, the switching controller is configured to control the drive coil switching circuit to switch a drive coil to which the drive coil driving unit is electrically connected to any of the plurality of drive coils when the degree of stability detected by the drive magnetic field generation control circuit is low.

9. The position detecting system according to claim 1, wherein the external device includes:
a plurality of the drive coil;
a drive coil switching circuit configured to switch a drive coil to which the drive coil driving circuit is electrically connected to any of the plurality of drive coils; and
a switching controller configured to control the drive coil switching circuit to switch a drive coil to which the drive coil driving circuit is electrically connected to any of the plurality of drive coils,
wherein the drive magnetic field generation control circuit is configured to output the degree of stability detected by comparing the difference with the reference value as a comparison result signal to the switching controller, and
wherein the switching controller controls the drive coil switching circuit to switch a drive coil to which the drive coil driving circuit is electrically connected to any of the plurality of drive coils when the comparison result signal indicates that the difference is larger than the reference value.

10. The position detecting system according to claim 1, wherein
the body-insertable apparatus includes a magnetic field generating circuit for generating a predetermined magnetic field,
the external device includes:
a guidance signal output circuit configured to output a guidance signal for generating a guidance magnetic field to control a position and a direction of the body-insertable apparatus, the guidance signal having a frequency different from the predetermined frequency, and
a guidance coil configured to receive the output guidance signal and to generate the guidance magnetic field in the detection space, and
wherein the guidance signal output circuit is configured to output the guidance signal to make the guidance coil generate the guidance magnetic field when the degree of stability of the drive magnetic field detected by the drive magnetic field generation control circuit is low.

11. The position detecting system according to claim 1, wherein:
the body-insertable apparatus includes a magnetic field generating unit for generating a predetermined magnetic field, and
the external device includes:
a guidance signal output circuit configured to output a guidance signal for generating a guidance magnetic field to control a position and a direction of the body-insertable apparatus, the guidance signal having a frequency different from the predetermined frequency, and
a guidance coil configured to receive the output guidance signal and to generate the guidance magnetic field in the detection space, and
wherein the guidance signal output circuit is configured to output the guidance signal to make the guidance coil generate the guidance magnetic field when the degree of stability of the drive magnetic field detected by the drive magnetic field generation control circuit is high.

12. A method of detecting a position in a subject of a body-insertable apparatus including a resonance circuit for emitting a resonance magnetic field by being induced by a drive magnetic field received from the outside, the method comprising:

a drive magnetic field generating step of generating the drive magnetic field by inputting a drive signal having a predetermined frequency to a drive coil;

a resonance magnetic field detecting step of detecting the resonance magnetic field;

a position deriving step of deriving position information of the body-insertable apparatus from the resonance magnetic field detected in the resonance magnetic field detecting step;

a current detecting step of detecting a current amplitude value of the drive signal input to the drive coil; and a drive magnetic field generation control step of
calculating an amplitude value of a drive signal which is input to the drive coil on the basis of the current amplitude value,
detecting the degree of stability of the drive magnetic field on the basis of whether a sharp change occurs in the calculated amplitude value, and
controlling the deriving of the position information at the position deriving step on the basis of the detected degree of stability of the drive magnetic field.

13. The method of position detection according to claim 12, wherein
in the drive magnetic field generation control step, the difference between a previously calculated amplitude value and a currently calculated amplitude value is calculated and compared with a preset reference value, and
in the position deriving step, the resonance magnetic field detected in the resonance magnetic field detecting step or the position information derived in the position deriving step is validated or invalidated on the basis of a result of comparison between the difference and the reference value in the drive magnetic field generation control step.

14. The method of position detection according to claim 13, wherein the position deriving step includes
a position calculating step of deriving the position information on the basis of an average value of a first predetermined number of times of the resonance magnetic field detected in the resonance magnetic field detecting step; and
an average number increasing/decreasing step of increasing/decreasing the first predetermined number of times on the basis of a result of comparison between the difference and the reference value in the drive magnetic field generation control step.

* * * * *